United States Patent
Segalla et al.

(10) Patent No.: US 10,654,806 B2
(45) Date of Patent: May 19, 2020

(54) MENTHYL NICOTINATE SYNTHESIS PROCESS

(71) Applicant: MULTICHEM IP LLC, Clearwater, FL (US)

(72) Inventors: Gabriele Segalla, Peschiera del Garda (IT); Marco Segalla, Carpiano (IT)

(73) Assignee: MULTICHEM IP LLC, Clearwater, FL (US)

( * ) Notice: Subject to any disclaimer, the term of this patent is extended or adjusted under 35 U.S.C. 154(b) by 0 days.

(21) Appl. No.: 16/072,843

(22) PCT Filed: May 15, 2017

(86) PCT No.: PCT/EP2017/061635
§ 371 (c)(1),
(2) Date: Jul. 25, 2018

(87) PCT Pub. No.: WO2017/211543
PCT Pub. Date: Dec. 14, 2017

(65) Prior Publication Data
US 2019/0077759 A1 Mar. 14, 2019

(30) Foreign Application Priority Data

Jun. 7, 2016 (IT) .................. 102016000058282

(51) Int. Cl.
*C07D 213/803* (2006.01)
*B01D 3/10* (2006.01)

(52) U.S. Cl.
CPC ........... *C07D 213/803* (2013.01); *B01D 3/10* (2013.01); *B01D 2257/70* (2013.01)

(58) Field of Classification Search
CPC ............................................. C07D 213/803
See application file for complete search history.

(56) References Cited

U.S. PATENT DOCUMENTS 3,917,613 A * 11/1975 Unilever .............. A61K 8/4913
546/227
9,144,572 B2 9/2015 Segalla

FOREIGN PATENT DOCUMENTS

JP 48-005592 B 2/1973
JP 49-17579 B 5/1974

OTHER PUBLICATIONS

"Transesterification of Methyl Esters of Aromatic and α,β-Unsaturated Acids with Bulky Alcohols: (−)-Menthyl Cinnamate and (−)-Menthyl Nicotinate." Organic Syntheses, (1993) Coll. vol. 8, pp. 350; (1990) vol. 68, pp. 155. (Year: 1993).*
Charonnat et al., "Sur quelques esters nicotiques de mono et poly-alcools et leurs dérivés halogéno-alcoylés", Mémoires Présentés à la Société Chimique, 1948 (with English Translation of Relevant Statement).
Wikipedia contributors, "Fischer-Speier esterification.", Wikipedia, The Free Encyclopedia., (Jul. 24, 2018), Retrieved 19:18, Aug. 10, 2018 https://en.wikipedia.org/w/index.php?title=Fischer%E2%80%93Speier_esterification&oldid=851813289.
Meth-Cohn, "Transesterification of Methyl Esters of Aromatic and α,β-Unsaturated Acids with Bulky Alcohols: (−)- Menthyl Cinnamate and (−)-Menthyl Nicotinate",Organic Syntheses, Coll. vol. 8, p. 350 (1993); vol. 68, p. 155 (1990).
International Search Report and Written Opinion, dated Jul. 5, 2017, from corresponding PCT application No. PCT/EP2017/061635.

* cited by examiner

*Primary Examiner* — John S Kenyon
(74) *Attorney, Agent, or Firm* — Young & Thompson

(57) ABSTRACT

Disclosed is a process for preparing menthyl nicotinate with high purity and yield, which consists of a transesterification reaction of menthol with a $C_1$-$C_4$ alkyl ester of the nicotinic acid, in the presence of an alkaline catalyst belonging to the class of $C_1$-$C_4$ alkoxides, linear or branched, and a vacuum distillation of the mixture of reaction products, in the presence of activated carbons.

20 Claims, No Drawings

MENTHYL NICOTINATE SYNTHESIS PROCESS

The present invention relates to a new process of synthesis of menthyl nicotinate, with an industrially acceptable final yield of menthyl nicotinate at high purity, easily accomplished in a relatively short time and without the use of any type of solvent or of precursors or intermediate compounds or materials that are hazardous or difficult to handle or store.

Menthyl nicotinate (CAS Nbr 40594-65-8; EINECS 254-991-1) is the ester of menthol and of nicotinic acid, having the formula $C_{16}H_{23}NO_2$ and structure:

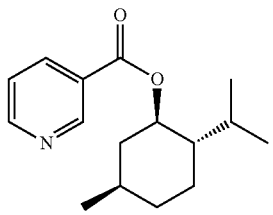 [SMILES: CC(C)[C@@H]1CC[C@@H](C)C[C@H]1OC(=O)c1cccnc1]

This molecule is an active ingredient used in cosmetics, for example in creams and gels for the treatment of cellulite, in lotions for the treatment of hair loss, in toothpastes and mouthwashes, as well as in topical preparations for the stimulation of sexual response thanks to its vasodilating properties (activating the cutaneous microcirculation).

See for example patents JP48005592B (Ito, Hiroo et al); U.S. Pat. No. 3,917,613 (Francoise Ernestine Lucie Humbert et al.); U.S. Pat. No. 9,144,572B2 (Segalla).

There are essentially three methods currently known for preparing an ester such as menthyl nicotinate:
1. Directly from carboxylic acids, according to the reaction of direct esterification, by making a specific carboxylic acid (i.e. nicotinic acid) to react with an alcohol (i.e. menthol) in the presence of a strongly acid dehydrating catalyst (commonly sulfuric acid or p-toluenesulfonic acid), usually either in an excess of alcohol which also serves as solvent, or in non-polar solvents (i.e. benzene, toluene). This is the most classical type of esterification, commonly known as Fischer-Speier esterification, as described for the first time by Emil Fischer and Arthur Speier in 1895 (Emil Fischer, Arthur Speier "*Darstellung der Ester*", Chemische Berichte 28: 3252-3258, 1895.).
2. From the chlorides of carboxylic acids (i.e. nicotinoyl chloride hydrochloride). The chloride of the specific carboxylic acid, usually in the presence of a weakly basic solvent, such as pyridine, reacts with the alcohol (i.e. menthol) producing the ester and developing hydrochloric acid.
See for example what is described in publication no. 206 of R. Charonnat, M. et J. V. Harispe L. et Chevillard "*Sur quelques esters nicotiques de mono et poy-alcools et leurs dérivés halogéno-alcoylés*", Mémoires Prësentés à la Société Chimique, 1948.
3. From the esters (i.e. a nicotinic ester) by trans-esterification, exploiting the ability of an alcohol to remove, under certain conditions, another alcohol from an ester. The transesterification process is catalysed both by acids (sulfuric acid or anhydrous hydrochloric acid) and by bases (usually the conjugate bases of the alcohol, known as alkoxides). See for example the U.S. Pat. No. 3,917,613 (Humbert et al.).

The first method is not usable for the synthesis of menthyl nicotinate, since the presence of aggressive acid catalysts, such as in fact concentrated sulfuric acid or p-toluenesulfonic acid, gives rise to immediate collateral dehydration of menthol and consequently to the formation of unwanted secondary compounds (menthenes, menthanes, menthene dimers, menthene trimers, etc.), difficult to separate from the mixture of products, which drastically reduce, if not even hinder, the formation of menthyl nicotinate, as well as impart an amber or dark brown colour to said mixture.

The presence of overly reactive catalysts can also cause the simultaneous degradation of the molecule of the nicotinic acid, giving rise to the formation of secondary nitrogen compounds, which are also coloured and malodorous, with a final yield of menthyl ester which is insignificant and industrially unacceptable.

Similarly, also the second method described above, albeit for different reasons, is not readily applicable to the synthesis of menthyl nicotinate, in that expensive, requiring long production times and involving again the use of extremely reactive, hazardous and toxic substances, such as for example nicotinoyl chloride and its precursor thionyl chloride $SOCl_2$, a highly corrosive and toxic compound even by inhalation only, and toxic solvents such as for example pyridine, benzene and trichloromethane, as well as the development of gaseous hydrochloric acid, also extremely aggressive, corrosive, toxic by inhalation and contact with skin and eyes.

In fact, this second method too, mainly due to the chemical aggressiveness of hydrochloric acid, can easily cause degradation of menthol, especially when not working at low temperatures. Furthermore the whole process, although characterised by an acceptable yield (79% according to the authors), however requires long production times and multiple reaction phases (preparation of nicotinoyl chloride and subsequent reaction of the latter with menthol), distillation and recovery of the solvents, washing with alkalized water, neutralisation of the acid, separation of the organic phase from the aqueous phase, drying, etc. that make it too complex industrially, not advantageous economically and too risky ecologically.

The third method of preparation as indicated above (transesterification) is the process that introduces less disadvantages for the synthesis of menthyl nicotinate. A method is known for example which consists in reacting menthol with the nicotinate of methyl alcohol (methyl nicotinate), in the presence of the sodium alkoxide of menthol (sodium mentholate) as catalyst obtained in situ, at the initial step of the process, by making metallic sodium pre-react with menthol, as described in U.S. Pat. No. 3,917,613.

However, even this third synthesis method has certain critical aspects that make it inapplicable industrially for the preparation of menthyl nicotinate, such as for example overly long reaction times of the metallic sodium with menthol, gaseous hydrogen formation (highly flammable and explosive), use of water for washing and subsequent separation of the organic phase by means of hazardous organic solvents such as methylene chloride (suspected of causing cancer), as well as a final yield that is too low (50%) to be acceptable for an industrial process on a large scale.

Another process of synthesis of menthyl nicotinate through transesterification is that reported by Organic Syntheses, Coll. Vol. 8, p. 350 (1993); Vol. 68, p. 155 (1990) "*Transesterificatlon of methyl esters of aromatic and α, β-unsaturated acids with bulky alcohols: (−)-Menthyl cin-*

*namate and (−)-Menthyl nicotinate,*" consisting essentially in making menthol to pre-react with n-butyllithium (n-BuLi), a strongly basic organometallic compound which, because of its instability to air, is normally supplied in organic solution (usually in hexane) and considered very dangerous, especially if it comes into contact with water, with which it releases gases which may ignite spontaneously.

Such reaction in fact, as indicated in detail by the authors of the publication, must take place in an absolutely anhydrous environment and in atmosphere consisting of an inert gas such as argon (i.e. isolated from the surrounding air, due to the high reactivity and incompatibility of n-butyllythium with water, oxygen and carbon dioxide), in a solvent consisting of tetrahydrofuran which is a highly volatile colourless liquid, with unpleasant characteristic odour, highly flammable and tending to form peroxides, which can decompose even violently, and for this reason usually inhibited with butylhydroxytoluene or stored in airtight bottles over sodium hydroxide.

The final yield reported by the authors is still good (77-83%), even if, in essence, such apparently high yield is mainly due to the fact that, in this specific case, n-butyllithium is not essentially employed as a catalyst (i.e. at low concentrations), but as an actual intermediate reagent, in quantities that are relatively very high, even almost stoichiometric with menthol (100 mmol menthol: 88 mmol n-butyllithium), for the express purpose of forming another reagent, lithium mentholate, which in turn reacts with the methyl ester bringing about the formation of menthyl nicotinate.

All this, however, is achieved at a cost that makes the entire process disadvantageous on an industrial scale (currently the price of 1 litre of n-butyllithium 1,6 M solution in hexane from Sigma-Aldrich is € 178.12 and the price of 8 litres is € 958.00).

The whole process is therefore more suitable to be carried out in a laboratory for purely academic purposes than feasible in industrial productions, taking into account also the fact that, in addition to the above described critical factors of an economic nature, it makes use of hazardous solvents and compounds that are toxic and difficult to store.

Furthermore, this preparation too requires numerous and complex phases of deaeration, dehumidification, continuous insufflation of argon, water washings, separation of the organic phase, drying, distillation, etc.

The object of the present invention is to overcome, at least in part, the prior art disadvantages by providing a synthesis process of menthyl nicotinate that is alternative, if not even improved, with respect to the known ones, both as regards yield and simplicity, speed, cost-effectiveness and eco-sustainability of all those operational and industrial phases which are necessary in order to obtain a product with a high degree of purity.

Another object is to provide a process characterized also by such a high yield so as to be advantageous from an industrial point of view for large-scale productions.

This, and other objects which will be disclosed here below, are achieved by the synthesis process according to the invention having the features listed in the appended independent claim 1.

Advantageous embodiments of the invention are disclosed by the dependent claims.

An object of the present invention relates to a process of synthesis of menthyl nicotinate with a final yield of menthyl nicotinate that is industrially acceptable and of high purity, which does not require the use of harmful solvents, comprising two steps: a transesterification reaction and a subsequent vacuum distillation in the presence of activated carbons.

More particularly, the synthesis process of the present invention comprises the following steps:

Step 1: Transesterification reaction of menthol with a $C_1$-$C_4$ alkyl ester (linear or branched) of the nicotinic acid (provided that this ester and the corresponding alcohol have a boiling point substantially lower than that respectively of menthyl nicotinate and of menthol, such as to be easily separable from their mixture by distillation), preferably a $C_1$-$C_2$ alkyl ester, more preferably methyl nicotinate, in the presence of an alkaline catalyst belonging to the class of alkyl alkoxides or alcoholates R—O-Me$^+$, where R is a $C_1$-$C_4$, preferably $C_1$-$C_2$, alkyl group, linear or branched, and where Me$^+$ is selected from sodium and potassium, more preferably said alkoxide being chosen from among sodium methoxide and potassium methoxide, even more preferably sodium methoxide, said alkoxide being present in a quantity preferably comprised between 0.1 and 10% (by weight with respect to the ester), and said menthol being in a molar ratio comprised between 1:1 and 20:1 with respect to said alkyl ester of the nicotinic acid, carrying out the reaction at a temperature comprised between 40-150° C., preferably between 70-120° C., according to the following diagram

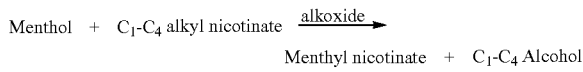

said transesterification reaction being carried out also in a partial vacuum, for example between 100 and 400 mbar, to facilitate the removal of all, and only, the $C_1$-$C_4$ alkyl alcohol which is produced by the reaction, filtering the final mixture obtained after distillation of said alkyl alcohol so as to separate the solid catalyst residue, consisting mostly of menthyl alkoxide, from the remaining liquid components.

Step 2—Distillation of the mixture obtained from step 1, in the presence of activated carbons, preferably, but not exclusively, powdered (PAC, powdered activated carbon), in a concentration of PAC with respect to the mass of product to be distilled comprised between 0.1 and 5% by weight, preferably between 0.3-1.2%, under conditions of temperature and vacuum such as to distil first the alkyl ester which has not reacted in step 1 and then the excess menthol (both constituting the forerunner that can be reused in the next processes) and subsequently the pure menthyl nicotinate.

In step 1 the $C_1$-$C_4$ alkyl ester reagent is in molar ratios preferably comprised between 1:1.5 and 1:2 with respect to menthol.

In a preferred embodiment of the invention, step 1 is performed by a transesterification reaction of menthol with methyl nicotinate in the presence of sodium methoxide, in order to more easily obtain the removal of the corresponding alcohol (methyl alcohol) which is formed in said step 1.

In step 2, the size, the porosity and the specific surface of the activated carbons (generally in the order of 500-2500 m$^2$/g, preferably about 1400 m$^2$/g) are essential factors, even if these parameters can be suitably selected as a function of the operating conditions (temperature, vacuum, speed and effectiveness of stirring of the entire mass to be distilled).

By way of example, purely informative but non-limiting, for the purposes of the present invention, mention can be made of the powdered activated carbons commercially known as "Norit CA1" or "Norit CAP Super" by Norit Italia SpA, but also granular (GAC, granular activated carbon) such as "Acticarbone NCL 1240" and "Acticarbone NCL 816" by CECA Italiana SpA.

The percentages of use of the GAC (usually in the order as 0.5-3% by weight) must be, for obvious reasons (smaller contact surface), higher than those of the PAC, but they too bring about excellent performances in step 2, as well as a possible easier separation and reutilization for the next process. Almost all the types of activated carbons commercially available today have in any case proved to be useful for the purposes intended by the present invention, even if those, in powder, commonly used for bleaching of vegetable oils, were found to be the most suitable.

The conditions of temperature and vacuum of 2 are for example about 100° C. and mbar for the distillation of the methyl nicotinate/menthol fraction and approximately 170° C. and high vacuum (0.5-2.0 mbar) for the distillation of menthyl nicotinate.

The distillation of step 2 can be carried out according to any distillation technique known in the art, for example fractional distillation, molecular distillation and the like.

In step 2, the mixture of reaction products to be subjected to distillation in the presence of activated carbons is mainly constituted, in the case of the preferred embodiment described above, of menthyl nicotinate, excess menthol, a small amount of methyl ester which has not reacted and secondary resinous compounds, and is usually yellow/amber/brown coloured depending on the quantity of secondary terpenic substances that are inevitably generated in step 1.

After the step 2 distillation in the presence of activated carbons, a small residue remains, which is subsequently eliminated, composed of impregnated activated carbons and resinous terpenic compounds having a boiling point higher than that of menthyl nicotinate.

The yield of menthyl nicotinate of the present process according to the invention is at least equal to 65%, preferably at least 79%, more preferably comprised between 83-87%.

The high yield of the present process is largely ascribable to the fact that it does not require those additional steps of neutralisation and/or washing with water and/or separation of the organic phase solubilized in volatile organic solvents (i.e. methylene chloride, diethyl ether, etc.), normally required in the art by other processes that use synthesis routes different from the present one.

The degree of purity of menthyl nicotinate obtained at the end of the present process, confirmed by GC-MS, was found to be at least 98.5%, preferably around 99.55% (the remaining 0.45% is pure menthol). Refractive index at 20° C.: 1.5074; B.P.: 168° C. (0.7 mbar); Specific gravity: 1.04 g/cc.

The distilled menthyl nicotinate so obtained is perfectly transparent white (colourless), almost odourless and does not contain secondary terpenic residues (as confirmed by GC-MS and colorimetric analyses).

The Applicant has surprisingly and unexpectedly found that the presence of such activated carbons during the distillation of the reaction product in stage 2 involves a considerable increase in yield, as well as allows the achievement of a very high purity, which otherwise would not be obtainable with the same distillation in the absence of activated carbons. In this regard, see the comparative example set forth below.

Without being bound to any theory, it is presumable that the acid pH of the activated carbons (usually around 2.0-3.5) is also one of the factors involved in the high yield of the present process since it contributes to the "neutralization" of any possible remaining alkaline residue of the catalyst used in step 1.

The chemical inertness and resistance of the activated carbons to high temperatures enables them to be used, with surprising advantages, in the step 2 distillation of menthyl nicotinate which, because of its very high boiling point (approx. 160° C. at 0.7 mbar), needs to be distilled in conditions of high temperature (about 150-170° C.) and high vacuum (0.5-2.0 mbar), as already described above.

Tests carried out by the Applicant have shown that at these temperatures and vacuum conditions in fact, if the activated carbons were not used in step 2, there would inevitably be the passage in the distillate of coloured terpenic substances, which, because of their intermediate boiling points (i.e. comprised between those of the menthol fraction and those of the menthyl ester fraction), would easily pass into the distillate receiving flask together with the tail fractions of menthol and the head fractions of menthyl nicotinate, with the consequent inevitable contamination (colouring) of the end product collected, forcing the operator, should he wish to obtain a purer and colourless product, to subject the distillate to further, lengthy and costly steps of fractional distillation, at the expense of the final yield of menthyl nicotinate.

It should be noted that, advantageously, neither in step 1 nor in step 2 described above is it necessary to use organic solvents or to wash the organic phase with water.

The whole process in fact does not require additional steps of neutralisation and/or separation of the organic phase by means of separatory funnels and/or subsequent dehydration by means of drying agents.

It should be noted in fact that the whole process of synthesis of menthyl nicotinate (step 1 reaction and step 2 distillation) described above in accordance with the invention is always carried out in anhydrous conditions and never requires the need for several washings with water and consequent separations of the organic phase.

In particular, in the entire process there is no need of using organic chemical solvents, no development of flammable or explosive gases, no washing operations (i.e. several time-consuming stages of vigorous stirring of the reaction products mixture in water and subsequent settling of the aqueous phase), no separation of the organic phase, no need for drying/dehydrating of the organic product. Advantageously with the present synthesis process, the nicotinic ester of menthol which is distilled off is completely anhydrous, with a very high degree of purity (>99.50%) and a very high chemical yield (>83%).

It is easy to understand how the availability of a synthesis method that is simple, rapid, economical, efficient (high yield) and with reduced environmental impact, such as that described in the present invention, results in considerable advantages in the reduction of costs and in the economization of industrial resources and production times.

To those skilled in the arts of industrial syntheses it will be easy to understand how the herein described method can be susceptible of secondary or partial modifications such as for example the use of different alkaline catalysts or other nicotinic acid esters as reagent esters or other quantitative proportions of reagents or catalyst with respect to the reagents or other types of activated carbons, all modifications, however, that would fall within the scope of the present invention.

Below are some illustrative but non-limiting examples of the present invention.

EXAMPLE 1

Step 1—Reaction 615.20 g (3.9 M) of menthol and 360.00 g (2.6 M) of methyl nicotinate are melted in a reactor equipped with a distillation column under vacuum. 24.80 g of alkaline catalyst are added, consisting of a solution of sodium methoxide (5.4 M solution in methanol; 30% by weight), easily available on the market (currently used, inter alia, in the industry of biodiesel synthesis).

The resulting mixture is stirred and gradually heated at 70-120° C., under a vacuum necessary and sufficient to distil off all the methyl alcohol (and only the methyl alcohol) that is generated by the reaction, generally around 100-400 mbar. The reaction proceeds very rapidly and is completed within a few hours.

When all the methyl alcohol has been removed, the reactor content is collected and filtered (in order to separate the reaction liquid products from the solid residue of the catalyst that can possibly be recovered for future reutilization).

Step 2—Distillation

The product of step 1 (mainly consisting of menthyl nicotinate, excess menthol, a small amount of methyl ester which has not reacted and secondary terpenic compounds), usually yellow/amber/brown-coloured (depending on the quantity of terpenic substances that have inevitably been formed during step 1), is poured directly into a rotary evaporator.

Before starting the distillation, a suitable quantity of powdered activated carbons is added. The optimum concentration of PAC in the total mass of product to be distilled was found to be 0.3-1.2% by weight.

The distillation is then carried out at conditions of temperature and vacuum such as to distil first a small percentage of methyl nicotinate which has not reacted in step 1, and then the excess menthol fraction followed finally by the pure menthyl nicotinate.

A small residue remains in the distillation pot, which is subsequently eliminated, mostly composed of impregnated activated carbons and resinous terpenic substances having a boiling point higher than that of menthyl nicotinate.

The menthyl nicotinate yield is found to be 83-87%. The degree of purity, confirmed by GC-MS, was equal to 99.55% (the remaining 0.45% is pure menthol).

Its appearance is: a perfectly transparent white (colourless), almost odourless liquid. Hazen colour value (Lange LICO-620 colorimeter, C/2°): 9. Refractive index at 20° C. (Abbe refractometer, 589 nm): 1.5074

EXAMPLE 2 (COMPARATIVE)

The procedure described in Example 1 is performed in the same manner, except with regard to the activated carbons, which are not employed.

A strongly yellow-coloured product is obtained, with pyridine odour, extremely impure, with a degree of purity lower than 99%. Hazen colour value: 131. Refractive index at 20° C.: 1.5053.

The present invention is not limited to the previously described particular embodiments, but numerous detailed modifications can be made, within the reach of the person skilled in the art, without thereby departing from the scope of the invention itself, as defined in the appended claims.

The invention claimed is:

1. A process for preparing highly pure menthyl nicotinate in the absence of hazardous solvents, said process comprising the following steps
    Step 1: transesterification reaction of menthol with a $C_1$-$C_4$ alkyl ester of nicotinic acid, in the presence of an alkaline catalyst belonging to the class of $C_1$-$C_4$ alkoxides, linear or branched, at a temperature comprised between 40° C. and 150° C., wherein menthol is in a molar ratio comprised between 1:1 and 20:1 with respect to said $C_1$-$C_4$ alkyl ester of nicotinic acid,
    said reaction being conducted under partial vacuum to facilitate the removal of $C_1$-$C_4$ alkyl alcohol which is formed by the reaction, and then separating out a residue of the catalyst via filtration to obtain a mixture of reaction products;
    Step 2—Distillation of the mixture of reaction products obtained from step 1, in the presence of activated carbons having a concentration between 0.1 and 5%, with respect to the mass of the mixture of reaction products to be distilled, under conditions of temperature and vacuum to distil firstly said $C_1$-$C_4$ alkyl ester of nicotinic acid that has not reacted in step 1, then the menthol that has not reacted in step 1 and subsequently the pure menthyl nicotinate.

2. The process according to claim 1, wherein in step 1 the $C_1$-$C_4$ alkyl ester of nicotinic acid is methyl nicotinate.

3. The process according to claim 1, wherein in step 1 the $C_1$-$C_4$ alkyl ester of nicotinic acid is in molar amounts comprised between 1:1.5 and 1:2 with respect to menthol.

4. The process according to claim 1, wherein the temperature of step 1 is between 70° C. and 120° C.

5. The process according to claim 1, wherein the vacuum in step 1 is between 100 and 400 mbar.

6. The process according to claim 1, wherein in step 1 the catalyst is sodium methoxide.

7. The process according to claim 1, wherein the activated carbons of step 2 is activated carbons powder, and wherein the activated carbons powder has a specific surface area generally in the order of 500-2500 $m^2/g$.

8. The process according to claim 1, wherein the temperature and vacuum for the distillation of menthyl nicotinate in step 2 are about 150-170° C. and 0.5-2.0 mbar.

9. The process according to claim 1, wherein the yield of menthyl nicotinate is at least 65%.

10. The process according to claim 1, wherein in step 1 the catalyst is used in amounts comprised between 0.1 and 10% by weight with respect to the $C_1$-$C_4$ alkyl ester of nicotinic acid.

11. The process according to claim 1, wherein the purity of menthyl nicotinate is about 99.55%.

12. The process according to claim 2, wherein in step 1 the $C_1$-$C_4$ alkyl ester of nicotinic acid is in molar amounts comprised between 1:1.5 and 1:2 with respect to menthol.

13. The process according to claim 2, wherein the temperature of step 1 is between 70° C. and 120° C.

14. The process according to claim 3, wherein the temperature of step 1 is between 70° C. and 120° C.

15. The process according to claim 2, wherein the vacuum in step 1 is between 100 and 400 mbar.

16. The process according to claim 3, wherein the vacuum in step 1 is between 100 and 400 mbar.

17. The process according to claim 4, wherein the vacuum in step 1 is between 100 and 400 mbar.

18. The process according to claim 9, wherein the yield of menthyl nicotinate is at least 79%.

19. The process according to claim 9, wherein the yield of menthyl nicotinate is in a range of 83-87%.

20. The process according to claim 7, wherein the activated carbons powder has a specific surface area of about 1400 m$^2$/g.

* * * * *